(12) United States Patent
Hashimoto et al.

(10) Patent No.: US 7,378,650 B2
(45) Date of Patent: May 27, 2008

(54) ION-MOBILITY SPECTROMETER AND ION-MOBILITY ANALYSIS METHOD

(75) Inventors: Yuichiro Hashimoto, Tachikawa (JP); Hideki Hasegawa, Tachikawa (JP); Izumi Waki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/882,419

(22) Filed: Aug. 1, 2007

(65) Prior Publication Data

US 2007/0290128 A1    Dec. 20, 2007

Related U.S. Application Data

(63) Continuation of application No. 11/072,267, filed on Mar. 7, 2005, now Pat. No. 7,265,345.

(30) Foreign Application Priority Data

Oct. 6, 2004    (JP)    ............... 2004-293191

(51) Int. Cl.
*H01J 49/40*    (2006.01)
*B01D 59/44*    (2006.01)

(52) U.S. Cl. ............ 250/286; 250/287; 250/281; 250/282; 250/292

(58) Field of Classification Search ........... 250/286, 250/287, 281, 282, 292
See application file for complete search history.

(56) References Cited

U.S. PATENT DOCUMENTS

| 4,238,678 A | 12/1980 | Castleman et al. |
| 5,338,931 A | 8/1994 | Spangler et al. |
| 6,348,688 B1 | 2/2002 | Vestal |
| 2002/0070338 A1 | 6/2002 | Loboda |
| 2002/0070339 A1 | 6/2002 | Clemmer |
| 2004/0011952 A1 | 1/2004 | Johnston et al. |
| 2006/0024720 A1* | 2/2006 | McLean et al. ............... 435/6 |

FOREIGN PATENT DOCUMENTS

JP    2004-504696    7/2001

OTHER PUBLICATIONS

Chinese Patent Office Action dated Dec. 14, 2007, in Chinese.
Siems, William F., et al, "Measuring the Resolving Power of Ion Mobility Spectrometers", Analytical Chemistry, vol. 66, No. 23, Dec. 1, 1994, pp. 4195-4201.
Blanchard, William C., "Using Nonlinear Fields in High Pressure Spectrometry", International Journal of Mass Spectrometry and Ion Processes, 1989, pp. 199-210.
Siems, William F., et al., "Measuring the Resolving Power of Ion Mobility Spectrometers", Analytical Chemistry, vol. 66, No. 23, Dec. 1, 1994.
European Search Report dated Nov. 22, 2006.

* cited by examiner

*Primary Examiner*—Nikita Wells
(74) *Attorney, Agent, or Firm*—Reed Smith LLP; Stanley P. Fisher, Esq.; Juan Carlos A. Marquez, Esq.

(57) ABSTRACT

There is provided an ion-mobility spectrometer. This apparatus includes the following configuration components: An ion source for generating first ions, a first drift unit for separating the first ions by flight drift times, an ion dissociation unit for generating second ions by dissociating the first ions separated, and a second drift unit for separating the second ions by flight drift times. Moreover, the first drift unit, the ion dissociation unit, and the second drift unit are located inside a chamber whose pressure is set at 10 mTorr or higher. This apparatus allows execution of low-cost and high-resolving-power ion separation and detection.

5 Claims, 7 Drawing Sheets

(CONVENTIONAL SCHEME)

(PRESENT SCHEME)

ION-MOBILITY SPECTROMETER AND ION-MOBILITY ANALYSIS METHOD

CROSS REFERENCE TO RELATED APPLICATIONS

This application is a Continuation of nonprovisional U.S. application Ser. No. 11/072,267 filed on Mar. 7, 2005 now U.S. Pat. No. 7,265,345. Priority is claimed based on U.S. application Ser. No. 11/072,267 filed on Mar. 7, 2005, which claims the priority of Japanese Application 2004-293191 filed on Oct. 6, 2004, all of which is incorporated by reference.

BACKGROUND OF THE INVENTION

1. Field of the Invention

The present invention relates to an ion-mobility spectrometer and an ion-mobility analysis method for analyzing ions ionized at an ion source.

2. Description of the Related Art

Ion mobility spectrometry has been widely used for gas detection such as explosive detection. In addition to ion detection method based on the ion mobility, a mass spectrometry method exists as ion detection method. In the ion mobility spectrometry, ion separation is performed by the ion mobility differences. Meanwhile, in the mass analysis method, the ion separation is performed by mass-to-charge ratios. Namely, these two methods differ fundamentally. In the ion mobility method, the separation is performed under a pressure of 10 mTorr or higher, where ions collide with gas molecule many times during the ion-separation time. This means that this method positively utilizes collision effects between the ions and the gas molecule. Meanwhile, in the mass analysis method, the separation is performed under a pressure of 1 mTorr or lower, where the collisions between the ions and the gas molecule are small in number during the ion-separation time.

In JP-A-2004-504696, the ion mobility method has been described in detail. According to the description in JP-A-2004-504696, assuming that electric field is constant, reach time T needed to go through the flight distance, L, is represented by (Expression 1). Here, let the ion mobility be K, voltage be V, and displacement distance be L, respectively.

$$T = L^2/(KV) \qquad \text{(Expression 1)}$$

Depending on ion species, values of the ion mobility K differ from each other. This makes it possible to separate the ion species by using reach times of the flight to the detector. The ion mobility has been widely utilized for such apparatuses as an explosives detection apparatus at an airport or the like.

In JP-A-2004-504696, the following method has been described. Namely, after separating the ions by using the ion mobility as described, ion dissociation is performed in a reaction chamber, and then the fragment ions after being dissociated are detected at a mass spectrometer such as time-of-flight mass spectrometer that operate in high-vacuum pressure. According to the description in JP-A-2004-504696, after the ions have been once separated by using the ion mobility, the ions separated are sequentially introduced into a reaction chamber such as a collision cell. Then, the ions introduced into the reaction chamber are sequentially introduced via collision dissociation or the like into the mass analysis unit such as a time-of-flight mass spectrometer. Here, it is possible to acquire two-dimensional mannered data (i.e., the first dimension: mass mobility by the ion mobility spectrometry of the ions before being dissociated, the second dimension: mass-to-charge ratio on the ions after being dissociated), which enhances the resolving power tremendously. An ion separation time by the ion mobility spectrometry is equal to about tens of ms (peak width: from a few hundreds µs to a few ms). In contrast thereto, a time needed for acquiring mass spectrum by TOF mass spectrometer in high vacuum is equal to 100 µs or less. This separation time difference allows each mass spectrum to correspond to some species separated by the ion mobility.

In U.S. Pat. No. 6,348,688, the following method has been described. Namely, after separating the ions by using the time-of-flight mass spectrometer, only specific ions are separated by voltage switching. After that, the specific ions separated are introduced into a collision-dissociation chamber, where ions are dissociated and convert fragment ions. Then, the fragment ions are subjected to the time-of-flight mass spectrometer once again. According to the description in U.S. Pat. No. 6,348,688, it is possible to acquire exceedingly high selectivity and abundant data (first-stage: mass-to-charge ratio before the dissociation by mass spectrometry, second-stage: mass-to-charge ratio after the dissociation by mass spectrometry).

SUMMARY OF THE INVENTION

In a technology described in Anal. Chem. 1994, 66, 4195-4201, a problem exists that the resolving power is low. In a sample containing a lot of matrix substances, typical resolving power (i.e., T/ΔT) of from (20 to 50), brings about an increase in baseline, thereby causing measurement errors of small amount species. Meanwhile, in the technologies described in JP-A-2004-504696 and U.S. Pat. No. 6,348,688, a problem common thereto exists that the cost will increase. The mass spectrometer requires a low pressure ($10^{-3}$ Torr or lower). This necessitates a plurality of differential pumping regions, thus requiring that an expensive vacuum pump be set in each differential pumping region. Also, in particular, the time-of-flight mass spectrometer used in the technologies described in JP-A-2004-504696 and U.S. Pat. No. 6,348,688 requires an even lower pressure ($10^{-5}$ Torr or lower), an expensive data storage system having a time resolving power of a few GHz, and the like. As a result, in contrast to the fact that the usual ion-mobility spectrometer apparatus costs about (20 to 100) thousand dollars, the analysis apparatuses in the methods described in JP-A-2004-504696 and U.S. Pat. No. 6,348,688 cost about (200 to 1000) thousand dollars, which is more expensive of substantially one order. It is an object of the present invention to provide an ion-mobility spectrometer which allows implementation of the low-cost and high-resolving-power of ion separation detection.

An ion-mobility spectrometer of the present invention includes an ion source for generating first ions, a first drift unit for separating the first ions by flight drift times (i.e., ion mobility of the first ions), an ion dissociation unit for generating second ions by dissociating the first ions separated at the first drift unit, a second drift unit for separating the second ions by flight drift times (i.e., ion mobility of the second ions), and a detector for detecting the second ions separated at the second drift unit. Moreover, the first drift unit, the ion dissociation unit, and the second drift unit are located inside substantially one and the same chamber, or are executed inside different chambers. Pressures inside these chambers are set in a range of the atmospheric pressure to a low-vacuum pressure of 10 mTorr or higher.

An ion-mobility spectrometer of the present invention includes an ion source for generating first ions, an ion dissociation unit for separating the first ions by flight drift times in a first direction, and generating second ions by dissociating the first ions separated, and an ion drift unit for separating the second ions by flight drift times in a second direction perpendicular to the first direction. Moreover, the ion dissociation unit and the ion drift unit are located inside substantially one and the same chamber, or are executed inside different chambers. Pressures inside these chambers are set in a range of the atmospheric pressure to a low-vacuum pressure of 10 mTorr or higher.

An ion-mobility analysis method of the present invention includes a step of generating first ions at an ion source, a first separation step of separating the first ions by flight drift times at a first drift unit, an ion dissociation step of generating second ions by dissociating the first ions separated at the first separation step, a second separation step of separating the second ions by flight drift times at a second drift unit, and a step of detecting by a detector the second ions separated at the second separation step. Moreover, the first separation step, the ion dissociation step, and the second separation step are executed inside substantially one and the same chamber, or are executed inside different chambers. Pressures inside these chambers are maintained in a range of the atmospheric pressure to a low pressure of 10 mTorr or higher.

An ion-mobility analysis method of the present invention includes a step of generating first ions at an ion source, an ion dissociation step of separating the first ions by flight drift times in a first direction, and generating second ions by dissociating the first ions separated, and an ion drift step of separating the second ions by flight drift times in a second direction perpendicular to the first direction. Moreover, the ion dissociation step and the ion drift step are executed inside substantially one and the same chamber, or are executed inside different chambers. Pressures inside these chambers are maintained in a range of the atmospheric pressure to a low pressure of 10 mTorr or higher.

The above-described configuration allows implementation of the ion-mobility spectrometer and method which are capable of making the low cost and the high resolving power compatible with each other.

According to the ion-mobility spectrometer and method of the present invention, as compared with the prior arts, it becomes possible to implement the lower-cost and higher-resolving-power ion detection.

Other objects, features and advantages of the invention will become apparent from the following description of the embodiments of the invention taken in conjunction with the accompanying drawings.

DETAILED DESCRIPTION OF THE INVENTION

Figure 1:
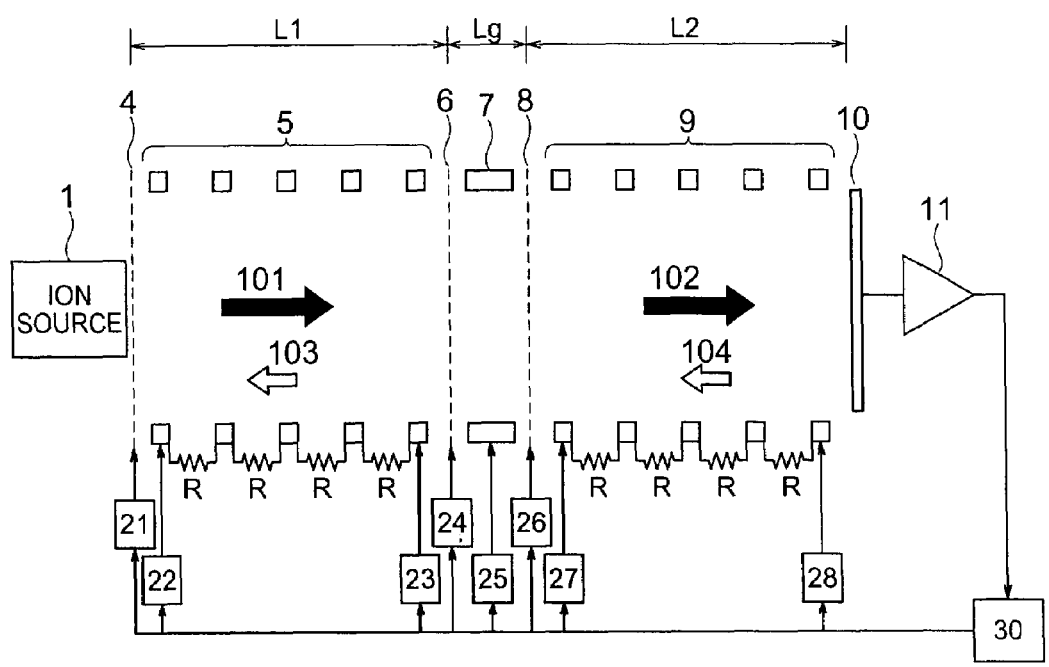
FIG. 1 is a diagram for illustrating configuration example of an ion-mobility spectrometer according to a first embodiment of the present invention.

The ion-mobility spectrometer of the present invention has characteristics such as: (1) the chambers are located under the atmospheric pressure, (2-1) the first ions are dissociated by maintaining temperature of the ion dissociation unit at 250° C., or higher, (2-2) the ion dissociation unit includes a light irradiation unit, and the first ions are dissociated by the light irradiation, (2-3) the ion dissociation unit includes an electron-beam irradiation unit, and the first ions are dissociated by the electron-beam irradiation, (3) the ion dissociation unit traps the first ions in more than 1 ms, (4-1) the ion-accelerating direction in the first drift unit and the ion-accelerating direction in the second drift unit are the same direction, (4-2) the ion-accelerating direction in the first drift unit and the ion-accelerating direction in the second drift unit are perpendicular to each other, and also, there are provided a plurality of detectors arranged in an array-like manner and used for detecting the second ions which have passed through the second drift unit.

The ion-mobility analysis method of the present invention has characteristics such as: (1) the first separation step, the ion dissociation step, and the second separation step are executed inside one and the same chamber located under the atmospheric pressure, (2-1) the ion dissociation step generates the second ions by dissociating the first ions at the ion dissociation unit via the heat dissociation whose temperature is equal to 250° C. or higher, (2-2) the ion dissociation step includes a light irradiation step, and the first ions are dissociated by the light irradiation at the ion dissociation unit, (2-3) the ion dissociation step includes an electron-beam irradiation step, and the first ions are dissociated by the electron-beam irradiation at the ion dissociation unit, (3) the ion dissociation step includes a step of trapping the first ions in more than 1 ms, (4-1) the ion-accelerating direction at the first separation step and the ion-accelerating direction at the second separation step in the first drift unit are the same direction, (4-2) the ion-accelerating direction at the first separation step and the ion-accelerating direction at the second separation step in the first drift unit are perpendicular to each other, and also, there is provided a step at which the second ions are detected by a plurality of detectors arranged in an array-like manner.

Hereinafter, referring to the drawings, the detailed explanation will be given below concerning embodiments of the present invention.

FIRST EMBODIMENT

FIG. 1 is a diagram for illustrating configuration example of an atmospheric-pressure ion-mobility spectrometer according to a first embodiment of the present invention.

Figure 2:
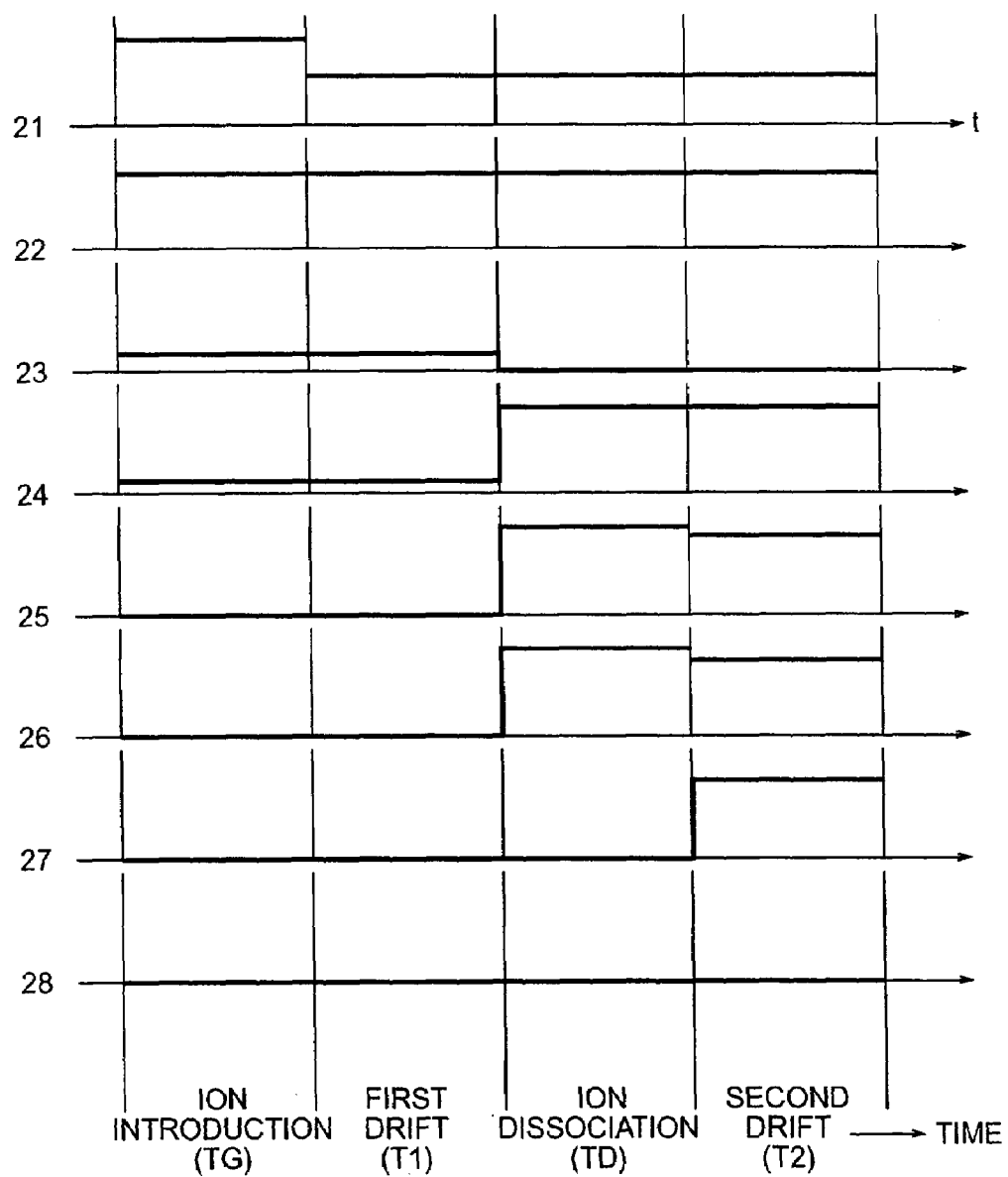
FIG. 2 is a diagram for explaining applied voltages to respective electrodes in respective sequences in the apparatus according to the first embodiment.

FIG. 2 is a diagram for explaining applied voltages to respective electrodes in respective sequences in the apparatus according to the first embodiment.

Figure 3:
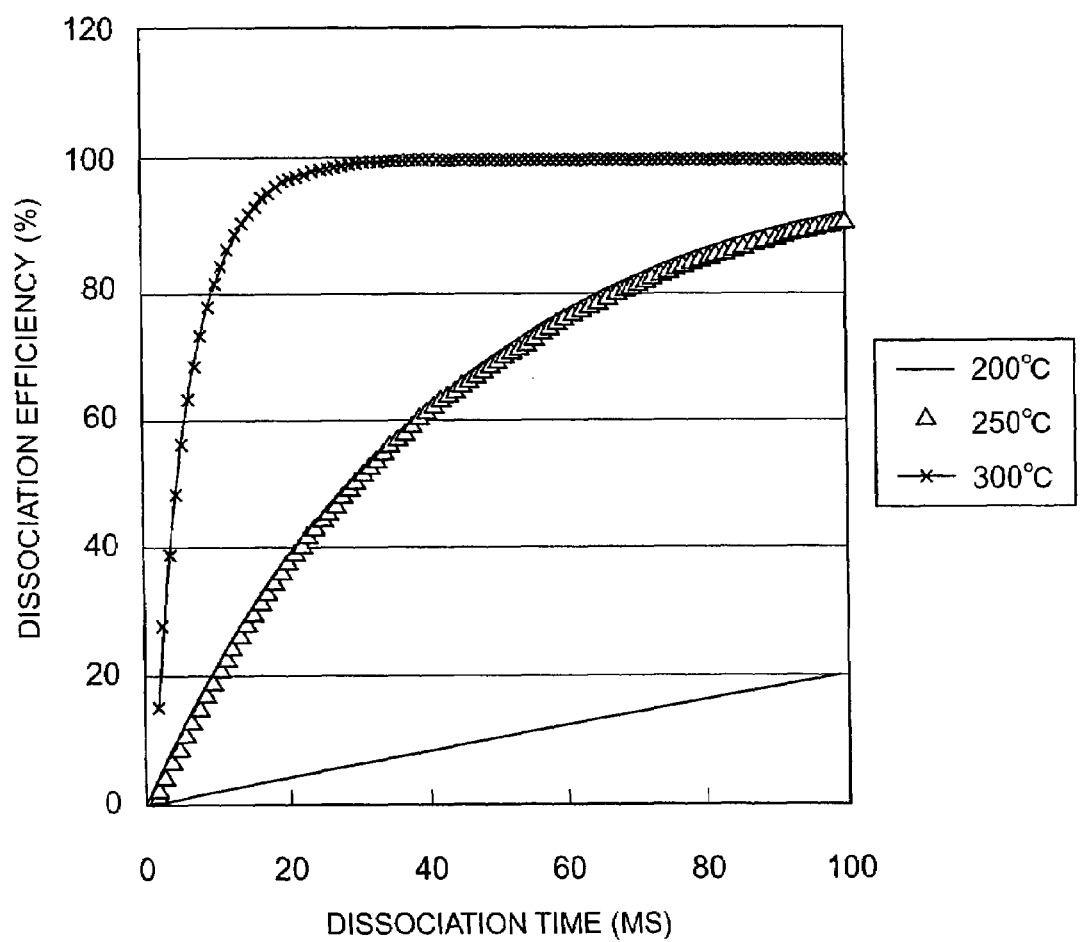
FIG. 3 is a diagram for explaining heat dissociation efficiency (calculation value) in the apparatus according to the first embodiment.

FIG. 3 is a diagram for explaining heat dissociation efficiency (calculation value) in the apparatus according to the first embodiment.

Figure 4A:
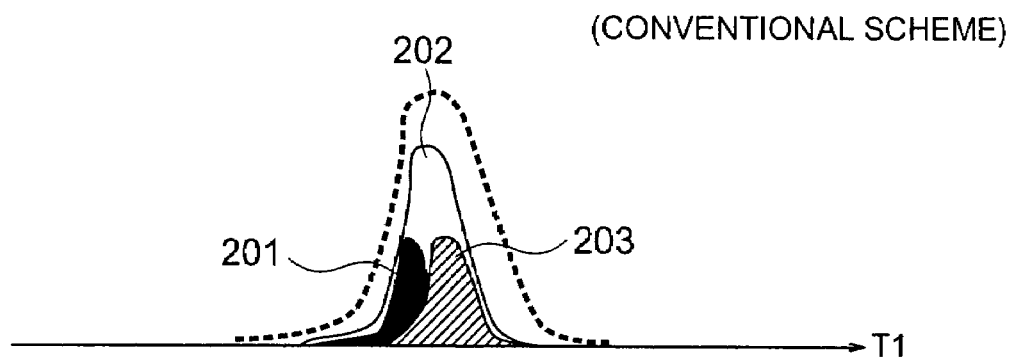
FIG. 4A and FIG. 4B are conceptual diagrams for explaining effects by the apparatus according to the first embodiment.
Figure 4B:
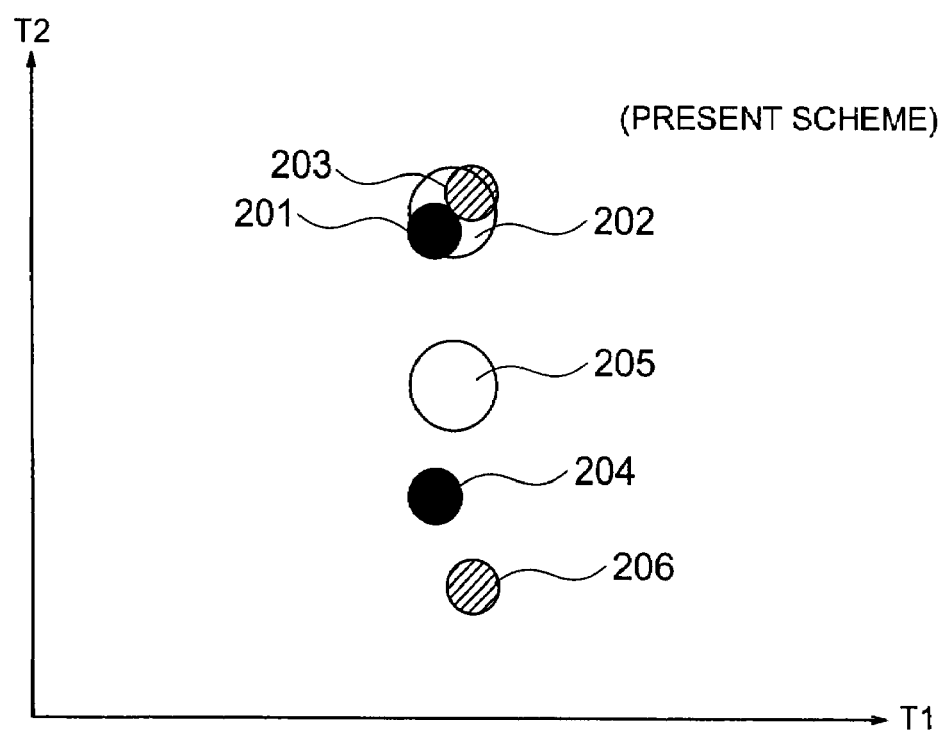

FIG. 4A and FIG. 4B are conceptual diagrams for explaining effects by the apparatus according to the first embodiment.

Measurement made by the ion-mobility spectrometer according to the first embodiment includes an ion introduction sequence of introducing first ions generated at an ion source 1 into a first drift region (unit), a first drift sequence of separating the first ions by flight drift times at the first drift region, an ion dissociation sequence (hereinafter, referred to as merely "dissociation sequence") of generating second ions at an ion dissociation unit by dissociating the first ions separated at the first drift region, and a second drift sequence of separating the second ions by flight drift times at a second drift region (unit).

At the sequence of introducing the first ions into the first drift region, switching of the voltage at a gate electrode 4 is performed. This switching allows the ions generated at the atmospheric-pressure ion source 1 to be introduced into the first drift region. Here, the first drift region is surrounded by the gate electrode 4, first acceleration electrodes 5, and an entrance-side mesh electrode 6. Ion introduction time (Tg) is set at about (100 to 500) μs. The longer Tg becomes, the more largely ion introduction quantity increases and thus sensitivity increases. However, there occurs a problem that initial time width increases and thus resolving power is lowered. Since resistance division is implemented between respective electrodes of the first acceleration electrodes 5, a substantially uniform acceleration electric-field is formed inside the first drift region. This electric field, in the first drift region, accelerates the ions in an ion acceleration direction 101. Meanwhile, in a gas flow direction 103 in the first drift region (which is the direction opposite to the ion acceleration direction 101 in the first drift region), and in a gas flow direction 104 in the second drift region (which is the direction opposite to an ion acceleration direction 102 in the second drift region), a gas such as dried nitrogen is introduced from a gas introduction aperture not illustrated in FIG. 1. This is performed for the purpose of suppressing contamination from ion sources or other electrodes and formation of water cluster generation.

Length L1 of the first drift region (i.e., distance between the gate electrode 4 and the entrance-side mesh electrode 6) is equal to about (4 to 20) cm. First drift voltage V1 (about (1 to 5) kV) is applied therebetween. At this time, ion displacement velocity v is represented by (Expression 2).

$$v = K(V1/L1) \quad \text{(Expression 2)}$$

Here, notation K denotes ion mobility specific to ion species, and is equal to about (1 to 5) cm$^2$/Vs. In the case where V1=2500V, L1=10 cm, and K=2 cm$^2$/Vs, the velocity v becomes equal to v=500 cm/s. According to (Expression 1), flight time T1 becomes equal to T1=25 ms. The ion introduction time (Tg) is set at the value which is short enough as compared with the first drift time (T1), because initial time width increases and thus resolving power is lowered. Except for influences of initial time width, resolving-power-degrading factors such as ion diffusion during the flight time, the resolving power by the ion mobility is limited to 50 or less. Therefore, the ion introduction time (Tg) is set at the value which is 1/50th or less of the first drift time T1 (=25 ms) (i.e., 500μs or less). Incidentally, as is shown from (Expression 1), T1 has different values for ions having different mobility.

Next, as illustrated in FIG. 2, the voltages applied to the respective electrodes are changed. This change makes it possible to selectively perform ion dissociation of only the ions existing within the ion selective-trap unit (i.e., the ion dissociation unit, the length: Lg). Here, the ion selective-trap unit is surrounded by the entrance-side mesh electrode 6, a trap electrode 7, and an exit-side mesh electrode 8. Ions with large ion mobility (i.e., high-speed ions) pass through the selective-trap unit, thus reaching the exit-side mesh electrode 8 and losing the charges. Meanwhile, ions with small ion mobility (i.e., low-speed ions), after starting of ion dissociation time, cannot exceed potential of the entrance-side mesh electrode 6, thus reaching the peripheral electrodes and losing the charges.

Incidentally, in FIG. 1 and FIG. 2, the reference numerals denote the following configuration components: 21a power-supply used for the gate electrode, 22 a power-supply entrance used for the first acceleration electrodes, 23 a power-supply exit used for the first acceleration electrodes, 24 a power-supply used for the entrance-side mesh electrode, 25 a power-supply used for the trap electrode, 26 a power-supply used for the exit-side mesh electrode, 27 a power-supply entrance used for the second acceleration electrodes, and 28 a power-supply exit used for the second acceleration electrodes.

During the ion dissociation period, the voltage application illustrated in FIG. 2 allows only the ions having the specific ion-mobility range to be selectively trapped into the ion dissociation unit (i.e., the selective-trap unit). The ion dissociation time Td is equal to about (1 to 20) ms, and in the meantime, the ions selectively trapped into the ion dissociation unit will be dissociated.

As dissociation methods, there can be considered methods such as heat dissociation, collision dissociation by collision, and ion-molecule dissociation using a reactive gas. Considering safety or the like, using the reactive gas is inadvisable. Also, electron-capture dissociation and optical dissociation result in high cost. The collision dissociation advances efficiently under a gas pressure of 10 Torr or lower. This is attributed to the fact that a high collision frequency occurring under the atmospheric pressure makes it impossible to supply sufficient ions' kinetic energy.

From the above-described reasons, the optimum method for the dissociation under the atmospheric pressure is the heat dissociation. The heat dissociation is the dissociation method available not only under the atmospheric pressure but also under a high-vacuum pressure. In order to apply effective gas heating to the ion dissociation unit alone, lamp heating is especially effective. Reaction rate τ in the case of the heat dissociation is represented by (Expression 3).

$$\tau = (1/A)\mathrm{Exp}(Ea/RT) \quad \text{(Expression 3)}$$

Here, notation A is referred to as "pre exponential factor", and is equal to about $10^{11} s^{-1}$ which substantially corresponds to oscillation frequency. Typical ion dissociation energy Ea is equal to about (100 to 200) kJ/mol (about (1 to 2) eV).

FIG. 3, which is the diagram for explaining effects of the present invention, indicates calculation value of heat dissociation efficiency in the case where Ea=100 kJ and A=$10^{11} s^{-1}$ are assumed. Transverse axis indicates the dissociation time (ms), and longitudinal axis indicates the heat dissociation efficiency (%).

As illustrated in FIG. 3, the effective gas heating results in the following heat dissociation efficiency, for example: At the dissociation time 20 (ms), 4.4% at 200° C., 37% at 250° C., and 96% at 300° C. At the dissociation time 30 (ms), about 10% at 200° C., about 50% at 250° C., and almost 100% at 300° C. Namely, at 300° C., almost 100-% ions are dissociated at the dissociation time 30 (ms). In whatever dissociation techniques, it is essential to trap the ions within the ion dissociation unit in more than a few ms. At the time of the trapping, two points, i.e., diffusion of the ions and influences of the gas flow, become problems. Considering the case of a 10-ms trapping time, typical diffusion spread-width is equal to 0.5 mm. This does not exert much influence on the separation after the trapping by the second ion mobility. Meanwhile, the gas flow is equal to, typically, about (1 to 5) mm/10 ms. This, in some cases, exerts much influence thereon. In particular, if the dissociation continues to be performed over a long time, it is effective to prevent the ions from being influenced by the gas flow and to stop the ions. This is performed by applying the direct electric-field in the direction opposite to that of the gas flow. After the dissociation has been performed, direct electric-field is applied inside the selective-trap unit, thereby introducing the dissociated ions into the second drift region including the exit-side mesh electrode 8 and the second acceleration electrodes 9.

Length L2 of the second drift region is set at basically the same order of the length L1 of the first drift region, and second drift voltage V2 is set at basically the same order of the first drift voltage V1. Having passed through the second drift region, the ions reach a detector 10 one after another. Output signal from the detector, after being amplified by an amplifier 11, is stored as the data (T1, T2, signal intensity) into a controller 30 including a PC (personal computer) or the like.

Total time necessitated for the ion introduction sequence (Tg), the first drift sequence (T1), the dissociation sequence (Td), and the second drift sequence (T2) become equal to, typically, about 50 ms in total. These sequences of about (10 to 50) different T1-time patterns in which T1 is changed are repeated. Assuming that the measurement is performed using the sequences of 20-way different time patterns with different T1, the whole measurement time of 20-way different-T1 analysis becomes equal to 1s. The apparatus configuration according to the first embodiment allows the ion mobility before the dissociation and the ion mobility after the dissociation to be acquired for all the ions in about 1 s. From the ion-mobility spectrum data before the dissociation (T1) and after the dissociation (T2), it becomes possible to accomplish the separation power (30×30=900) which was impossible to be accomplished by the conventional ion-mobility method.

FIG. 4A and FIG. 4B illustrate ion separation schematic in the conventional scheme and ion separation schematic in the embodiment of the present invention, respectively.

In the prior arts in FIG. 4A, if T1 is substantially equal to each other in actual samples, a signal 201 resulting from an ion type A, a signal 202 resulting from an ion type B, and a signal 203 resulting from an ion type C overlap with each other. This makes the accurate measurement impossible. In the first embodiment of the present invention, however, the re-separation is performed after the ion dissociation. This makes it possible to implement a two-dimensional mapping as is illustrated in FIG. 4B. In this case, the ion type A, the ion type B, and the ion type C with substantially equal T1 before the dissociation, produce specific fragment ions which result from the ion species A, B, and C respectively and whose T2 and ion mobility differs from each other. Then, these fragment ions generate a signal 205 resulting from the ion type A after being dissociated, a signal 206 resulting from the ion type B after being dissociated, and a signal 207 resulting from the ion type C after being dissociated. This allows the separation of these ions after being dissociated, thereby resulting in an enhancement in the separation capability.

Incidentally, in the first embodiment, any one of the following configurations is allowable: Three of the first drift unit, the ion dissociation unit, and the second drift unit are located inside one and the same chamber, or any two of the three units are located inside one and the same chamber, or the three units are located inside different chambers each. Also, it is advisable that pressures inside the respective chambers fall in a range of 10 mTorr to the atmospheric pressure, and the pressures inside the respective chambers may be whether identical or different. Furthermore, in order to allow the ion dissociation to develop sufficiently, it is preferable that residence time of the first ions in the ion dissociation unit be made longer than residence time thereof in the first drift unit.

SECOND EMBODIMENT

Figure 5:
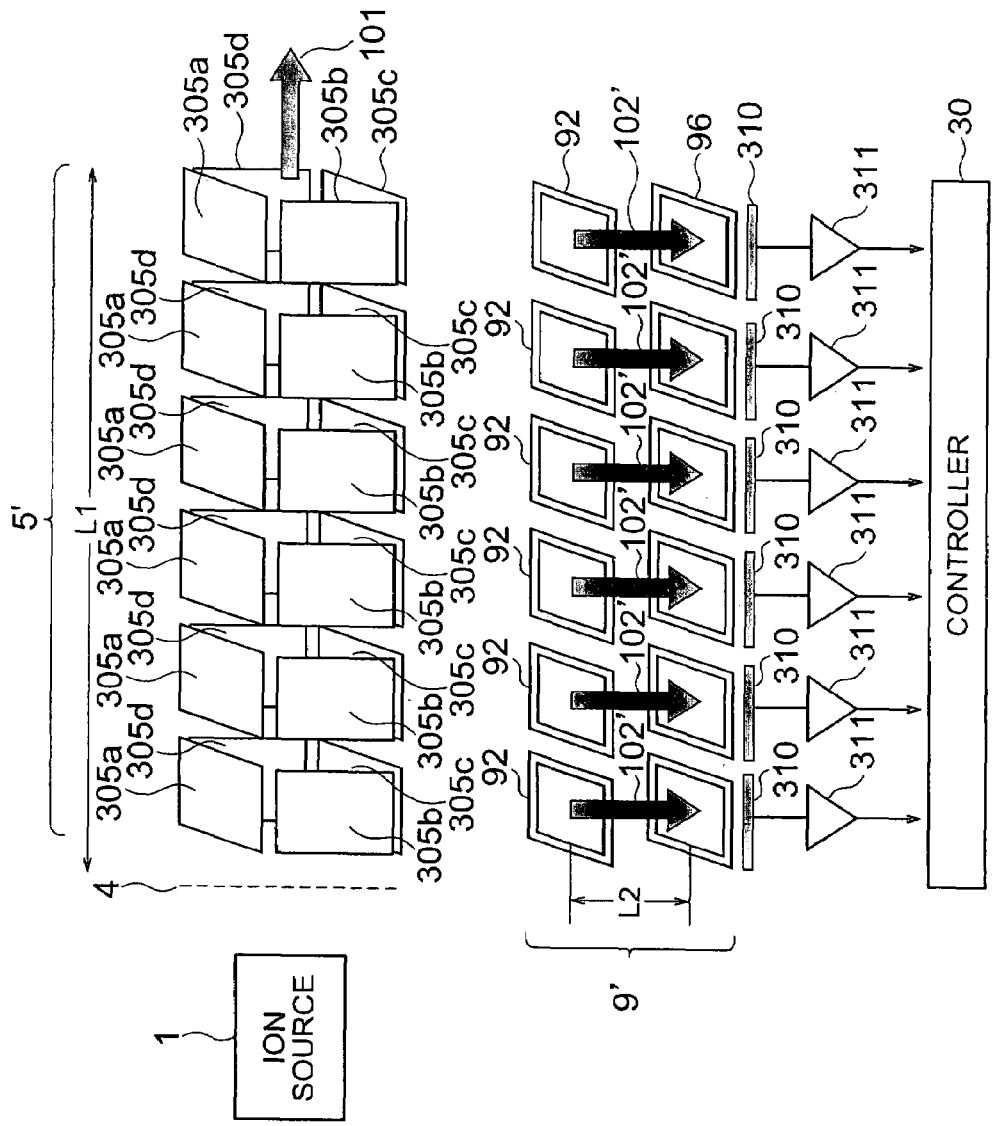
FIG. 5 is a diagram for illustrating configuration example of an ion-mobility spectrometer according to a second embodiment of the present invention.

FIG. 5 is a diagram for illustrating configuration example of an atmospheric-pressure ion-mobility spectrometer according to a second embodiment of the present invention.

Figure 6A:
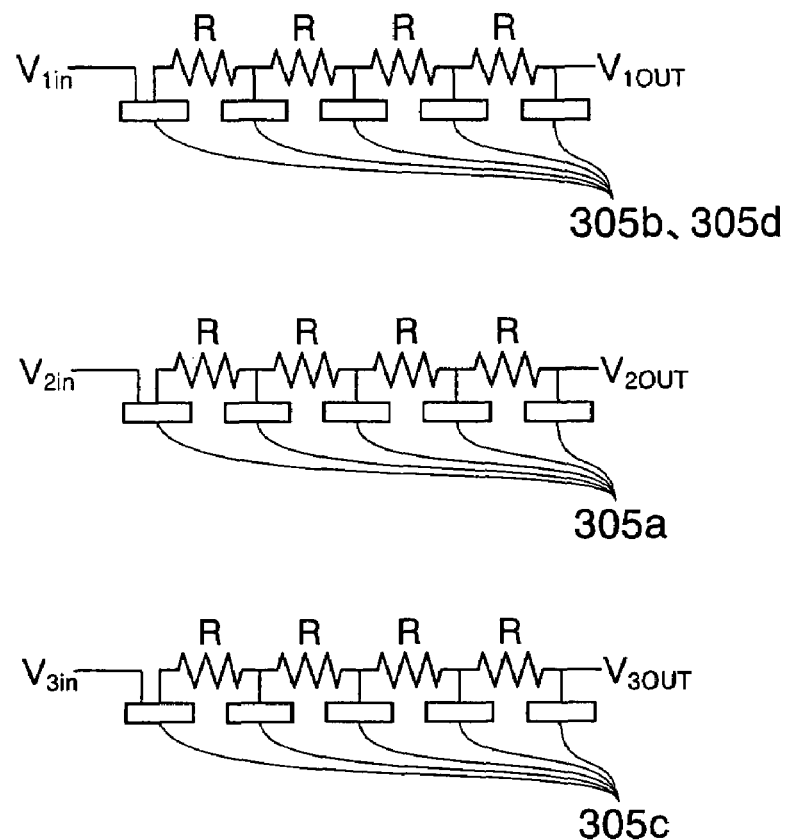
FIG. 6A, FIG. 6B, and FIG. 6C are diagrams for explaining configuration of acceleration electrodes in the apparatus according to the second embodiment, and applied voltages to respective electrodes in respective sequences therein.
Figure 6B:
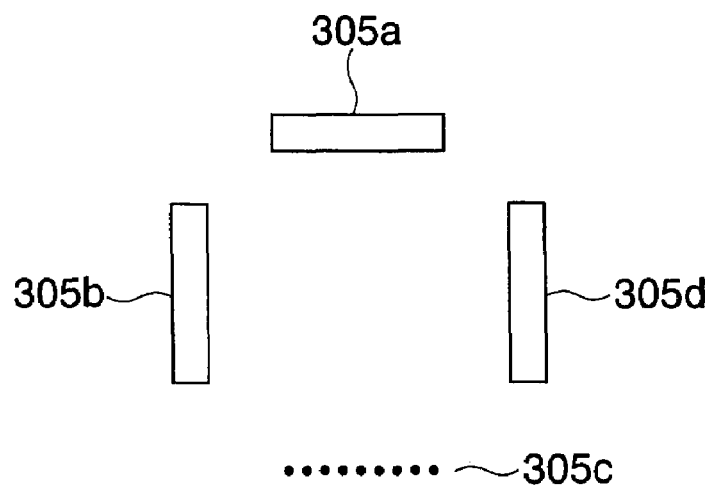
Figure 6C:
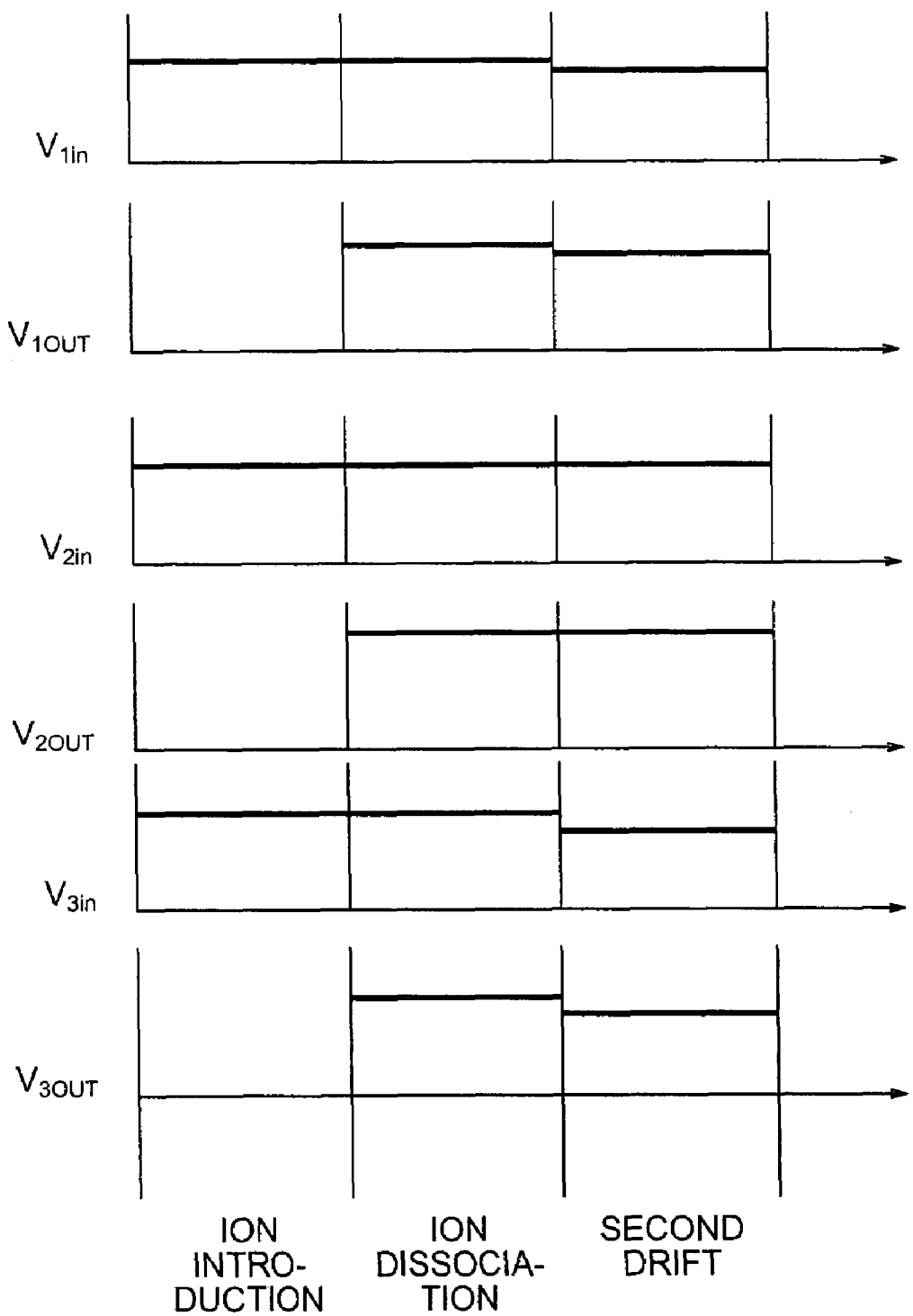

FIG. 6A, FIG. 6B, and FIG. 6C are diagrams for explaining configuration of acceleration electrodes in the apparatus according to the second embodiment, and applied voltages to respective electrodes in respective sequences therein. FIG. 6A and FIG. 6B are the diagrams for illustrating the configuration and lay-out of the acceleration electrodes 305a, 305b, 305c, and 305d of array-configured acceleration electrodes 305. FIG. 6C is the diagram for illustrating the applied voltages to the respective electrodes in the respective sequences (i.e., ion introduction sequence, first drift sequence, ion dissociation sequence, and second drift sequence) in the apparatus according to the second embodiment.

In the second embodiment, the explanation will be given below concerning the configuration of improving the throughput and sensitivity of the first embodiment. In the first embodiment, it has necessitated about is to acquire the one set of signal intensity data for the sequences of the set values of one combination of T1 and T2 illustrated in FIG. 2. In the configuration example illustrated in FIG. 5, however, it becomes possible to shorten this time by a tremendous amount.

Switching of the voltage at a gate electrode 4 is performed. This switching allows ions generated at an atmospheric-pressure ion source 1 to be introduced into a first drift region (unit), thereby allowing performance of the first drift sequence. Here, the first drift region is surrounded by the gate electrode 4 and the first acceleration electrodes 5', i.e., the array-configured acceleration electrodes 305 (which include the plurality of combinations of acceleration electrodes 305a, 305b, 305c, and 305d, and which are arranged in an ion acceleration direction 101 in the first drift region (the length: L1)). Then, the ions are accelerated in the ion acceleration direction 101 inside the array-configured acceleration electrodes 305. The ion species are separated in space along the ion acceleration direction 101 by ion-mobility differences. Similarly to the first embodiment, as illustrated in FIG. 6A, resistance division is implemented between the respective acceleration electrodes 305a, 305b, 305c, and 305d of the first acceleration electrodes 5'. Accordingly, a substantially uniform acceleration electric-field is formed inside the first drift region. This electric field, in the first drift region, accelerates the ions in the ion acceleration direction 101.

Next, during about (2 to 10) ms, the ions continue to drift. After that, direct-current voltages are changed so that the electric field inside the array-configured acceleration electrodes 305 will be made equal to zero (if a gas flow exists inside the array-configured acceleration electrodes 305, an electric field is applied in a direction opposite to that of the gas flow, so that ions can be trapped therein). This makes it possible to trap the ions inside the array-configured acceleration electrodes 305. Temperature of this inside portion is maintained at 200° C. or higher in order to allow the ion dissociation to develop efficiently.

In the first embodiment, the first and second drift regions and the ion selective-trap unit (i.e., the ion dissociation unit) differ from each other. In the configuration of the second embodiment, however, most of the first drift region is used as the ion selective-trap unit (i.e., the ion dissociation unit) for selectively trapping the ions to perform the ion dissociation. This results in a new problem that the ion dissociation will advance in the first drift sequence too. Prevention of this phenomenon requires that the time for the ion dissociation sequence be made much longer as compared with the time for the first drift sequence. Namely, the time T1 for the first drift sequence is set at about 5 ms, which is comparatively short. Meanwhile, the time Td for the ion dissociation sequence is set at 20 ms or more, which is much longer. This setting allows the ion ratio dissociated within the time for the first drift sequence to be suppressed down to a low value.

As ion dissociation methods, in addition to heat dissociation, there can be considered methods such as collision dissociation by collision, electron-capture dissociation by electron beam or the like, optical dissociation by light, and ion-molecule dissociation using a reactive gas. In these ion dissociation methods, however, there exist problems similar to those explained in the first embodiment. After performing the ion dissociation by using any one of the ion dissociation methods, direct-current voltages are applied to the inside of the ion dissociation unit (i.e., the array-configured acceleration electrodes 305) in the second embodiment. This accelerates the ions in an ion acceleration direction 102' in the second drift region which is perpendicular to the ion acceleration direction 101 inside the array-configured acceleration electrodes 305.

At this time, as illustrated in FIG. 6A, FIG. 6B, and FIG. 6C, a DC voltage is applied between the acceleration electrodes 305a and 305c. As illustrated in FIG. 6B, using a mesh electrode as the acceleration electrode 305c is advisable for ion transmittance. FIG. 6C illustrates applied states in the respective sequences of an acceleration-electrode-use power-supply entrance voltage $V1_{in}$ for the acceleration electrodes 305b and 305d, an acceleration-electrode-use power-supply exit voltage $V1_{out}$ for the acceleration electrodes 305b and 305d, an acceleration-electrode-use power-supply entrance voltage $V2_{in}$ for the acceleration electrode 305a, an acceleration-electrode-use power-supply exit voltage $V2_{out}$ for the acceleration electrode 305a, an acceleration-electrode-use power-supply entrance voltage $V3_{in}$ for the acceleration electrode 305c, and an acceleration-electrode-use power-supply exit voltage $V3_{out}$ for the acceleration electrode 305c which are illustrated in FIG. 6A.

The ions are accelerated by DC potential applied to the second acceleration electrodes 9'. Then, after passing through between each pair of a plurality of pairs of acceleration electrodes 92 and 96 configuring the second drift region (the length: L2), the ions reach elements of array-configured detectors 310 one after another. Signals detected at the respective array-configured detectors 310, after being each amplified by amplifiers 311, are stored as the data (channel number (which refers to number allocated to combinations of the acceleration electrodes 92 and 96, the elements of the array-configured detectors 310, and the amplifiers 311), T2, signal intensity) into a controller 30 including a PC or the like.

Times necessitated for one measurement including the ion introduction sequence (Tg), the first drift sequence (T1), the dissociation sequence (Td), and the second drift sequence (T2) become equal to, typically, about 50 ms in total. The channel number provides information on the ion mobility before the ion dissociation, and ion second drift time provides information on the ion mobility after the ion dissociation.

In the first embodiment, the one measurement including the ion introduction sequence (Tg), the first drift sequence (T1), the dissociation sequence (Td), and the second drift sequence (T2) has necessitated about is. In contrast thereto, in the second embodiment, it becomes possible to acquire the ion mobility in about 50 ms. This allows accomplishment in speeding-up by a tremendous amount. As compared with the first embodiment, shortening the ion first drift time somewhat lowers the resolving power in the first drift sequence, and lengthening the time for the ion dissociation sequence somewhat lowers the resolving power in the second drift sequence. In the second embodiment, however, it becomes possible to accomplish the separation power ($10 \times 20 = 200$) which was impossible to be accomplished by the ion mobility method in the prior arts.

Incidentally, in the second embodiment, either of the following configurations is allowable: Two of the ion dissociation unit and the ion drift unit are located inside one and the same chamber, or are located inside different chambers each. Also, it is advisable that pressures inside the respective chambers fall in a range of 10 mTorr to the atmospheric pressure, and the pressures inside the respective chambers may be whether identical or different. Furthermore, in order to allow the ion dissociation to develop sufficiently, it is preferable that residence time of the first ions in the ion dissociation unit be made longer.

Incidentally, although not illustrated, gas chromatographs or respective types of temperature-raising gas separation apparatuses can be used at front-stage locations of the ion source in the apparatus of the present invention. In such a case, it is needless to say that the separation capability will be enhanced even further. This is because, in addition to the information on the ion mobility before and after the ion dissociation, gas-introducing time axes from these separation apparatuses are added.

According to the ion-mobility spectrometer and method of the present invention, it becomes possible to provide the ion-mobility spectrometer and method which are capable of making the low cost and the high resolving power compatible with each other.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An ion-mobility spectrometer, comprising:
   an ion dissociation unit for separating a first ion by flight drift times to generate a second ion by ion dissociation of said separated first ion, and
   an ion drift unit for separating said second ion by flight drift times
   wherein times for dissociating said first ion is longer compared to time for separating said first ion by said flight times at said ion dissociation unit.

2. An ion-mobility spectrometer according to claim 1, wherein the time for ion dissociation sequence of said first ion is set t 20 ms or more.

3. An ion-mobility spectrometer according to claim 1, wherein said ion dissociation unit is composed of a plurality of electrodes, and said plurality of electrodes are aligned in line with ion accelerating direction of said first ion.

4. An ion-mobility spectrometer according to claim 1, wherein ion dissociation of said first ion is heat dissociation.

5. An ion-mobility spectrometer according to claim 1, wherein the direction of ion acceleration at said ion dissociation unit is perpendicular to the direction of ion acceleration at said ion drift unit.

* * * * *